United States Patent [19]

Kasting, Jr. et al.

[11] Patent Number: 5,501,844

[45] Date of Patent: Mar. 26, 1996

[54] AIR TREATING APPARATUS AND METHOD THEREFOR

[75] Inventors: John R. Kasting, Jr., Waxhaw; Ronald G. Potter, Monroe, both of N.C.

[73] Assignee: OxiDyn, Incorporated, Monroe, N.C.

[21] Appl. No.: 251,466

[22] Filed: Jun. 1, 1994

[51] Int. Cl.$^6$ .................................................. B01J 19/12
[52] U.S. Cl. ............................. 422/186.15; 422/186.07; 422/907
[58] Field of Search ......................... 422/186.07, 907, 422/186.15

[56] References Cited

U.S. PATENT DOCUMENTS

| Re. 34,571 | 3/1994 | Uys | 422/186.07 |
|---|---|---|---|
| 2,326,601 | 8/1943 | Arff | 204/320 |
| 2,345,798 | 4/1944 | Daily | 204/318 |
| 3,565,776 | 2/1971 | Arff | 204/320 |
| 3,752,748 | 8/1973 | McMillan, Jr. | 204/157.1 R |
| 3,979,193 | 9/1976 | Sikich | 55/123 |
| 4,764,349 | 8/1988 | Arff et al. | 422/186.18 |
| 4,857,277 | 8/1989 | Broomfield | 422/186.07 |
| 4,863,701 | 9/1989 | McMurray | 422/186.08 |
| 4,904,289 | 2/1990 | Miyakami et al. | 62/157 |
| 4,909,996 | 3/1990 | Uys | 422/186.07 |
| 4,963,331 | 10/1990 | Mouw | 422/186.18 |
| 4,990,311 | 2/1991 | Hirai et al. | 422/4 |
| 5,124,132 | 6/1992 | Francis, Jr. et al. | 422/186.07 |

*Primary Examiner*—Donald P. Walsh
*Assistant Examiner*—Daniel Jenkins
*Attorney, Agent, or Firm*—Bell, Seltzer, Park & Gibson

[57] ABSTRACT

An air treating apparatus and method therefor is disclosed that can be used in spaces occupied by humans or other mammals for deodorizing the air with ozone while the humans or other mammals are present. A housing having an air inlet and an air outlet defining an air flow passageway therebetween has a fan in the inlet for drawing air through the passageway and discharging the air through the outlet. The housing contains a transformer for supplying high voltage electrical power to an ozone generator in the air passageway for enriching the air in ozone and discharging a mixture of ozone in the air at a predetermined concentration. A potentiometer controls a timer for controlling the interval over which ozone is produced in an "on/off" manner. The time averaged concentration of ozone thereby is controlled so that exposure to ozone does not exceed established limits over time.

10 Claims, 2 Drawing Sheets

AIR TREATING APPARATUS AND METHOD THEREFOR

FIELD OF THE INVENTION

This invention relates to methods and apparatus for treating air with ozone. More specifically, this invention relates to methods and apparatus for generating ozone from air and deodorizing the air.

BACKGROUND OF THE INVENTION

Ozone, or $O_3$, is an allotropic form of oxygen that exists as an unstable blue gas. Ozone readily is produced from air or other oxygen containing gas by passage of a high voltage electrical discharge through a stream of the oxygen-containing gas.

Ozone is an active oxidizing agent that destroys bacteria, viruses and other microorganisms on contact. Low levels of ozone are excellent for eliminating unpleasant odors in air, destroying pollen and dust particles, and even killing bacteria that may be floating in the air or on surfaces in contact with the air. Unlike many other disinfecting agents, ozone is used as it is generated, breaks down rapidly and does not leave chemical residues. Ozone reverts to oxygen with a half life that can be as much as several hours in the absence of oxidizable matter.

However, ozone can be toxic in sufficient concentrations over a sufficient period of time. Ozone at lower concentrations is considered substantially non-toxic but exposure to a sufficient amount over a prolonged period can produce adverse symptoms in humans and other mammals and can irritate the eyes, nasal passages, and throat. Exposure to ozone for short periods of time of up to about 10 minutes at levels of over 1 ppm does not typically produce symptoms. Low levels of ozone of less than 0.1 ppm normally can be tolerated indefinitely. Limits have been established by OSHA for exposure to ozone in air for breathing purposes of no more than 0.1 ppm over an 8 hour period.

Various apparatus and methods have been proposed for using ozone to purify the air in living spaces and the like and to avoid exposure of humans and mammals to levels of ozone concentration that can cause problems. Many of the proposed devices have drawbacks in operation or construction that detract from their utility.

For example, McMurray U.S. Pat. No. 4,863,701 discloses an apparatus for generating ozone for deodorizing an enclosed space. A fan supplies a stream of air past ozone generating tubes to emit a stream of ozone enriched air from the apparatus. Excessive ozone production is counteracted by an odor emitting chamber. The chamber is located downstream of the fan and after the ozone producing cycle is complete and the undesired odor eliminated, the chamber can emit a conventional air freshening odor, a perfume, that reacts with excess ozone. The chamber can be operated on a timed cycle to release the perfume after ozone production ceases so that the deodorized space does not retain a high ozone concentration after ozone production ceases. The perfume releasing device is said to guarantee that the environment that is to be occupied immediately after ozone treatment is free of potential harmful concentration of residual ozone that normally can result from ozone treatments. Thus, it is clear that the device disclosed in McMurray is not intended for use in a space occupied by humans or other mammals during ozone treatment.

Uys U.S. Pat. No. RE. 34,571 discloses an apparatus for generating ozone for use as a deodorizer and air purifier within a predetermined area. The device includes a blower unit for supplying air to an ozone generating unit. The ozone generating unit discharges ozone into the air that is supplied. A separate mixing chamber that contains air is connected to receive the air supplied from the ozone generator and containing ozone. The ozone containing air and the relatively high volume of air in the mixing chamber are mixed, the ozone concentration in the air is thereby reduced, and the ozone and excess air mixture are discharged to the surrounding atmosphere by a second blower.

Miyakami et al. U.S. Pat. No. 4,904,289 discloses a deodorizing apparatus for use in a closed chamber such as a refrigerator or the cabin of an automobile. The device is discussed in connection with a refrigerator and Miyakami shows a case having an air inlet and an air outlet and an air flow channel disposed between the air inlet and the air outlet. The inlet and the outlet to the case are separately provided with a deodorizing catalyst for accelerating decomposition of odors and ozone and minimizing leakage of any residual ozone from the case into the refrigerator compartment.

The efficiency of the deodorizing catalyst gradually decreases, which permits residual ozone to flow out from the case into the refrigerator and results in an increased ozone concentration. The ozone generator is said to be driven intermittently to maintain the interior ozone concentration below a regulation value so that the interior ozone concentration does not exceed a regulation value of 0.1 ppm before 20 years.

Perfume releasing devices, catalysts, air mixing chambers, and the associated mechanical and electronic equipment for such features for controlling exposure to ozone can be costly. These features introduce complexity to the devices and result in additional possibilities for equipment failure. Devices that are intended for use only in the absence of people and other mammals and animals are restricted in their use and may not be effective or suitable for treating air in areas that frequently are occupied for extended periods and may be subject to a variety of odors.

SUMMARY OF THE INVENTION

The invention is based on the recognition that sufficiently high levels of ozone can be continually maintained for effectively treating air while simultaneously maintaining an average concentration over time of ozone in the air such that the air is suitable for breathing for an extended period. The invention provides an elegantly simple and relatively inexpensive method and apparatus for using ozone to deodorize air in environments such as hospitals, hotels, nursing homes, isolation rooms, dog and cat kennels, examining rooms, and other areas that are routinely occupied by people or other mammals and animals and that are subject to continual odor formations from body excretions and contamination by air borne microbes.

The apparatus can be placed in a room or other localized environment in a suitable location so that the occupants are not likely to come within a predetermined distance of the apparatus. The apparatus can be operated to deodorize the air circulated throughout the environment without exposing human or animal occupants present during the treatment of the air to concentrations of ozone that are toxic or substantially likely to produce adverse symptoms of ozone exposure. The apparatus can be operated in unoccupied spaces to produce higher concentrations of ozone suitable for an increased level of purification, if desired.

In one embodiment, the invention provides an apparatus for treating air with ozone. The apparatus includes a housing having an air inlet and an air outlet that defines a passageway for the passage of air through the apparatus. A means is provided for drawing air through the passageway from the inlet to the outlet and for discharging air through the outlet. A means is also included for continually introducing ozone into the air in the passageway for discharge through the outlet at a predetermined first concentration in the air at the outlet and for a predetermined period of time. The means can be adjusted to provide in the air surrounding the apparatus an average concentration of ozone over time that is not more than a predetermined average concentration for a given time period and a concentration of ozone in the air outside the apparatus during ozone production that is not more than a predetermined second concentration at a distance of not less than a predetermined distance from the housing.

In a more specific embodiment, the ozone introducing means includes a means for generating ozone that is located in the passageway. A means is provided for controlling the ozone generating means to produce ozone at a predetermined first concentration of from about 0.5 to 8 ppm. A means is also provided for controlling the interval of time over which the ozone generating means generates ozone for introduction into the air. These means, adjusted for the size of the room to be treated and the level of contamination in the room, control the average concentration over time of the ozone in the air outside the apparatus and control the concentration of ozone in the air outside the apparatus during ozone production at not more than a predetermined second concentration at a distance of not less than a predetermined distance from the housing.

In still more specific embodiments, a corona tube having a cathode is surrounded by a perforated jacket anode and provides ozone at a predetermined first concentration of from about 0.5 to 2 ppm of ozone in the air. Power is supplied to the generator from a transformer that has a predetermined secondary or output voltage of from about 8,000 to 12,000 volts. An on/off cycling timer relay electrically connected to the transformer cycles the transformer on and off at predetermined intervals set by an operator of the apparatus to control ozone production so that the maximum concentration of ozone in the air in the localized area surrounding the housing is not more than a predetermined second concentration of from about 0.2 to 0.4 ppm of ozone at a predetermined distance from the outlet of the housing of not less than about 2 feet. The average concentration over time of the ozone in the air surrounding the apparatus is not more than about 0.1 ppm over an eight hour period.

The invention also includes a method for treating air with ozone. The method comprises the steps of drawing air through a passageway, supplying electrical power at a predetermined voltage to enrich the air in the passageway in ozone at a predetermined first concentration, and discharging the ozone enriched air from the passageway. Electrical power is supplied to generate ozone in a controlled on/off cycle to provide a concentration of ozone in the air that is not more than a predetermined second concentration at a distance of not less than a predetermined distance from the passageway. The average concentration over time of the ozone in the air surrounding the apparatus is not more than a predetermined average concentration.

In still more specific embodiments, the air is drawn through the passageway at the rate of from about 50 to 60 cubic feet per minute ("cfm") and the on/off cycle is controlled at about 1 minute on and 10 minutes off. Power is supplied to a single generator at the level of about 9,000 volts. Air is enriched in ozone at a predetermined first concentration of about 1.0 to 1.5 ppm. The concentration of ozone in the air is not more than a predetermined second concentration of 0.2 to 0.4 ppm at a distance of not less than a predetermined distance of 2 feet from the passageway. The average concentration over time of the ozone in the air surrounding the apparatus is not more than a predetermined average concentration of 0.1 ppm over 8 hours.

Thus, the invention provides an apparatus and a method for deodorizing air in a space that is regularly occupied by human or animal occupants and can remain occupied during the ozone treatment. Average concentrations of ozone of over about 0.1 ppm over an 8 hour period can be avoided. Nevertheless, ozone concentrations are generated that are sufficient to purify the air of noxious odors and of contaminants that may be air borne or present on surfaces such as draperies, furniture, and linens. Adverse symptoms of ozone exposure in humans and animals are avoided by maintaining a distance of humans and other animals of about 2 feet from the outlet of the apparatus.

BRIEF DESCRIPTION OF THE DRAWINGS

For a more complete understanding of this invention, reference should now be had to the embodiment illustrated in greater detail in the accompanying drawings and described below in an example of the invention. In the drawings.

DETAILED DESCRIPTION OF THE INVENTION

Figure 1:
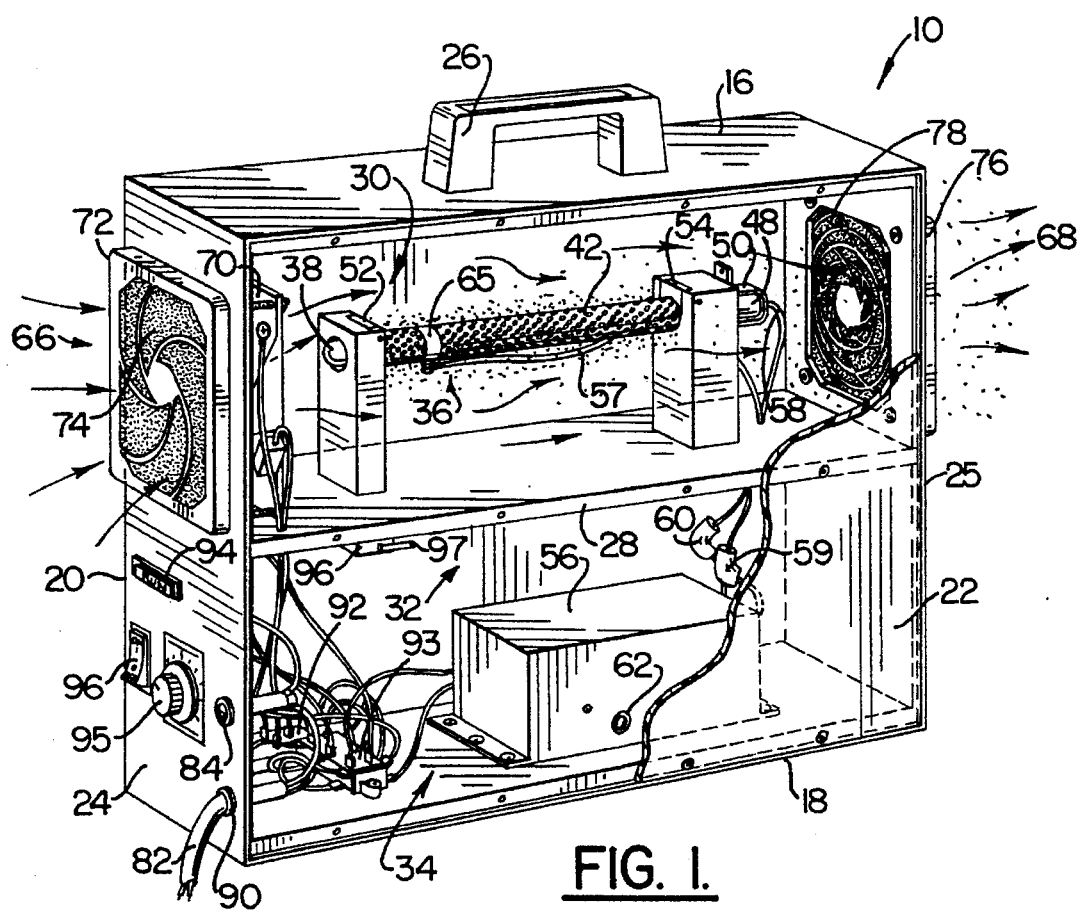
FIG. 1 represents a perspective view taken from the front, top and left side of an apparatus of the invention, including the external controls, and showing the internal components in a partially broken away view.

FIG. 1 shows generally at 10 a portable air purification unit for deodorizing a localized area in a veterinary clinic such as a waiting room or kennel that can be occupied by humans or other animals during ozone treatment of the air in the localized area. Operation of the unit effectively removes contaminants including odors from body excretions, smoke, hydrocarbon residues, yeasts, mold spores, pollen, bacteria, and viruses.

A housing 12 is fabricated from a machined, thermoformed, polyvinyl chloride ("PVC") plastic assembly. The housing 12 comprises top and bottom panels 16 and 18, front and rear panels 20 and 22, and end panels 24 and 25, all of PVC. PVC is relatively easy and economical to fabricate, resistant to ozone oxidization, relatively easily cleaned, has excellent strength to weight characteristics, provides insulation from electrical components, and has an attractive appearance for use in medical and other facilities. The housing can be formed of other materials that are resistant to ozone oxidation and would be suitable for use in the practice of the present invention, such as stainless steel sheet metal or other plastics.

Top panel 16 includes a handle 26 to provide a convenient means for lifting and transporting the unit. The unit represented in the drawings and as discussed herein weighs about 25 lbs. A PVC shelf 28 divides the housing into two compartments, an upper compartment 30 and a lower compartment 32 of approximately equal size, and provides support for the components of the upper compartment. Another PVC shelf 34 is located on the bottom panel of the housing and provides support for attachment of components in the lower compartment. Shelves 28 and 34 are attached using industrial strength adhesives.

Figure 2:
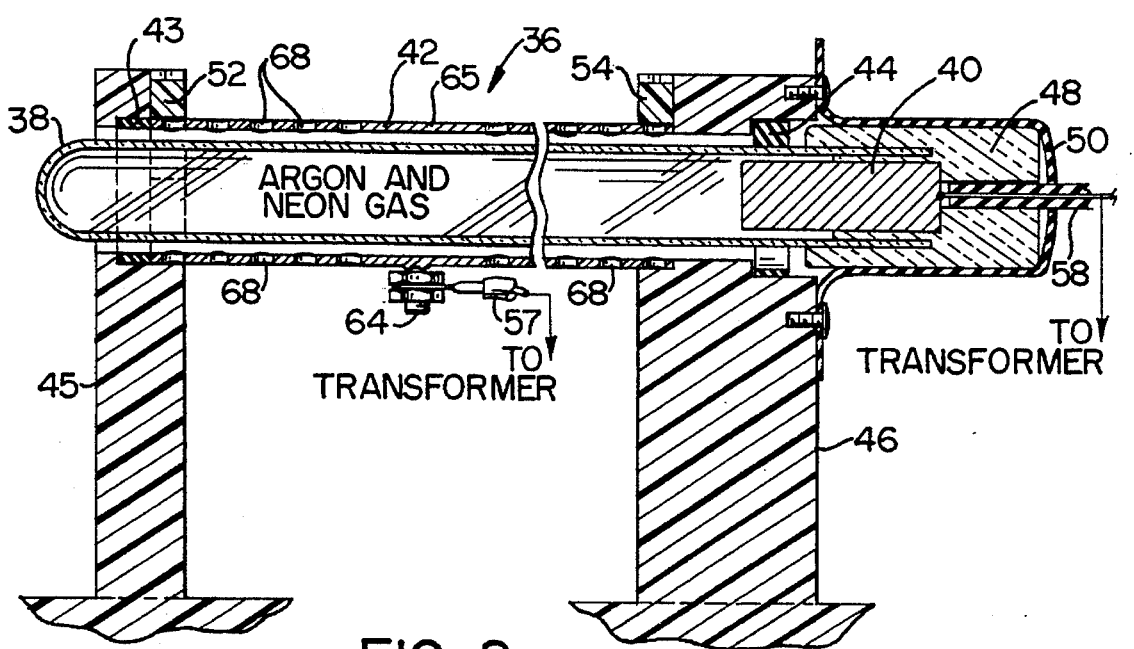
FIG. 2 shows a longitudinal section through a portion of the apparatus of FIG. 1.

The rear panel of the housing is partially broken away to show the interior components of the housing. An ozone generator 36 is fixedly mounted in the upper compartment for generating ozone and supplying ozone to an air stream that is moving through the housing as shown by the directional arrows. The ozone generator is a corona discharge generator that does not introduce potentially harmful substances into the air for circulation and purification. In the illustrated embodiment (FIG. 2), a single mercury-free corona lamp 38, which is a glass tube dielectric, contains a mixture of gases suitable for an ozone generator cathode, typically argon and neon gases. The cathode lamp contains a central, cylindrical, metallic, resistance heater element 40 for heating the gases in the tube and for excitation of the atoms of the gases in the tube for generating the corona. A corona lamp of the type used in the ozone generator of the invention is available from LCD Lighting, Inc., Milford, Conn.

A perforated annular stainless steel jacket anode electrode 42 surrounds the glass tube. The jacket electrode comprises a shell of perforated stainless steel sheet metal having unperforated edge portions and an unperforated central portion 65. The sheet metal has been rolled to form a cylinder and welded along its length to seal the seam. The perforations 68 in the jacket electrode provide for efficient cooling of the generator from the heat that is produced.

An air gap separates the corona lamp and the jacket electrode. The corona lamp is retained in place in the jacket electrode, radially centered and spaced from the jacket electrode, by silicon retainer rings 43 and 44 having axially directed spaces for the passage of air through the gap between the glass tube and the jacket electrode. The silicon rings are resistant to ozone oxidation. Silicon retainer rings of the type described are available from Seal Jet, Inc., Charlotte, N.C.

The ends of the corona tube and stainless steel jacket electrode are mounted in machined apertures in substantially non-conductive blocks 45 and 46 that are formed of PVC and are secured to the PVC shelf 28. An additional corona lamp and jacket electrode can be mounted in the blocks and powered by the same transformer, if desired, to increase ozone output. The end of the corona tube that is electrically connected to the transformer is surrounded by a non-conductive ceramic block 48 for safety and is fastened to the supporting block by a flexible silicon strip 50. The mounting arrangement, including the silicone spacers 43 and 44, provides some flexibility and acts as a shock absorber so that if the unit is dropped, then the glass lamp is unlikely to be damaged.

The PVC blocks into which the corona tube and jacket are mounted include removable sections 52 and 54 for releasing the corona tube. Upon removal of these portions and the flexible strip, the corona tube can easily be removed from the mounting blocks for replacement.

A transformer 56 is shown in FIG. 1 in lower compartment 32 for converting input line voltage to higher voltage and for supplying high voltage to the ozone generator for creating ozone. The transformer preferably is an inductive, step-up, high voltage transformer that can receive as line voltage standard household current so that an operator conveniently and safely can plug the unit into a suitable wall outlet. A compensator for line voltage should be included so that output voltage to the generator is constant.

Transformer 56 includes an adjustment screw 62 that allows the secondary or output voltage to be set at the appropriate value as determined by the manufacturer at the time the air purifier is assembled for ozone production at a predetermined first concentration. It should be understood that the ozone concentration produced may vary at constant voltage depending on the temperature and humidity of the air and other factors. However, air in an interior, conditioned environment is not expected to vary widely in ozone producing characteristics.

Typically, the primary or input voltage to the input electrodes will be from 110 VAC to 120 VAC. A 120 VAC 50/60 cycle primary is preferred for most geographical locations. Secondary or output voltage from output electrodes for the lead wires 57 and 58 that are connected to the ozone generator may vary from about 8,000 volts to 12,000 volts. Neoprene jackets 59 and 60 are provided for placement on the high voltage output electrodes to reduce the risk of electrical shock to persons having access to the interior of the housing. Voltage much less than 8,000 volts typically does not generate sufficient ozone for deodorizing air; voltage of above about 12,000 volts typically produces arcing in the ozone generator and results in problems. Normally, secondary or output voltage will be about 9,000 volts from a 120 VAC 50/60 cycle primary coil.

The transformer may optionally include an electronic inverter assembly that increases the input frequency to an output or secondary frequency of between 400 and 500 hz. This higher frequency provides more efficient generation of ozone from the air passed between the electrodes to the generator. Preferred Electronic in Westfield, Mass. provides such a transformer.

From the secondary terminals of the transformer, power is directed through high voltage power lead 58 to the corona lamp resistance element 40. At the voltage imposed by the transformer, an electric field (corona) is established in the area between the corona lamp and the anode electrode jacket 42. The electric circuit is completed through the high voltage lead 57 that is connected to the anode electrode jacket by mechanical connection to a welded stud 64 mounted on the unperforated and centrally located band portion 65 of the anode and to a secondary terminal of the transformer.

Also shown in FIG. 1 are an air inlet 66 and an air outlet 68 defining a passageway through the upper compartment 36 of the apparatus and for passage of air between the jacket electrode and the corona tube for the generation of ozone. Ozone is represented in FIG. 1 as small dots. The air travels through the space between the corona tube and the jacket electrode and ozone exits through the perforations 68 in the jacket electrode and through the annular space between the cathode and anode to be carried by the air stream and discharged through the air outlet in the housing into the atmosphere surrounding the housing.

A fan 70 is disposed in the air inlet. A fan finger guard assembly 72 and a relatively coarse open-celled foam filter 74 are provided on the exterior of the housing on the side panel 24 and mounted over the fan and air inlet. The outlet 68 is also covered by a guard 76 and filter 78 similar to the guard and filter on the inlet.

The outlet guard assembly and filter can easily be removed in the event that corona tube replacement becomes necessary. As described hereinabove, the corona tube can be removed from the mounting blocks. The tube is easily withdrawn through the air outlet and replaced.

Locating the fan in the inlet helps reduce the possibility of ozone damage to the fan. If located in the outlet, the fan would be more subject to exposure to ozone. The fan should be capable of moving sufficient air to generate ozone and to circulate and process the air in the environment to be treated. Typically, the fan should be rated to move from about 25 to 150 cubic feet per minute of air. For most typical size waiting rooms in clinics and the like, a fan that can move 50 to 60 cubic feet per minute should be sufficient. The fan shown in the drawing is rated at 57 cfm.

Figure 3:
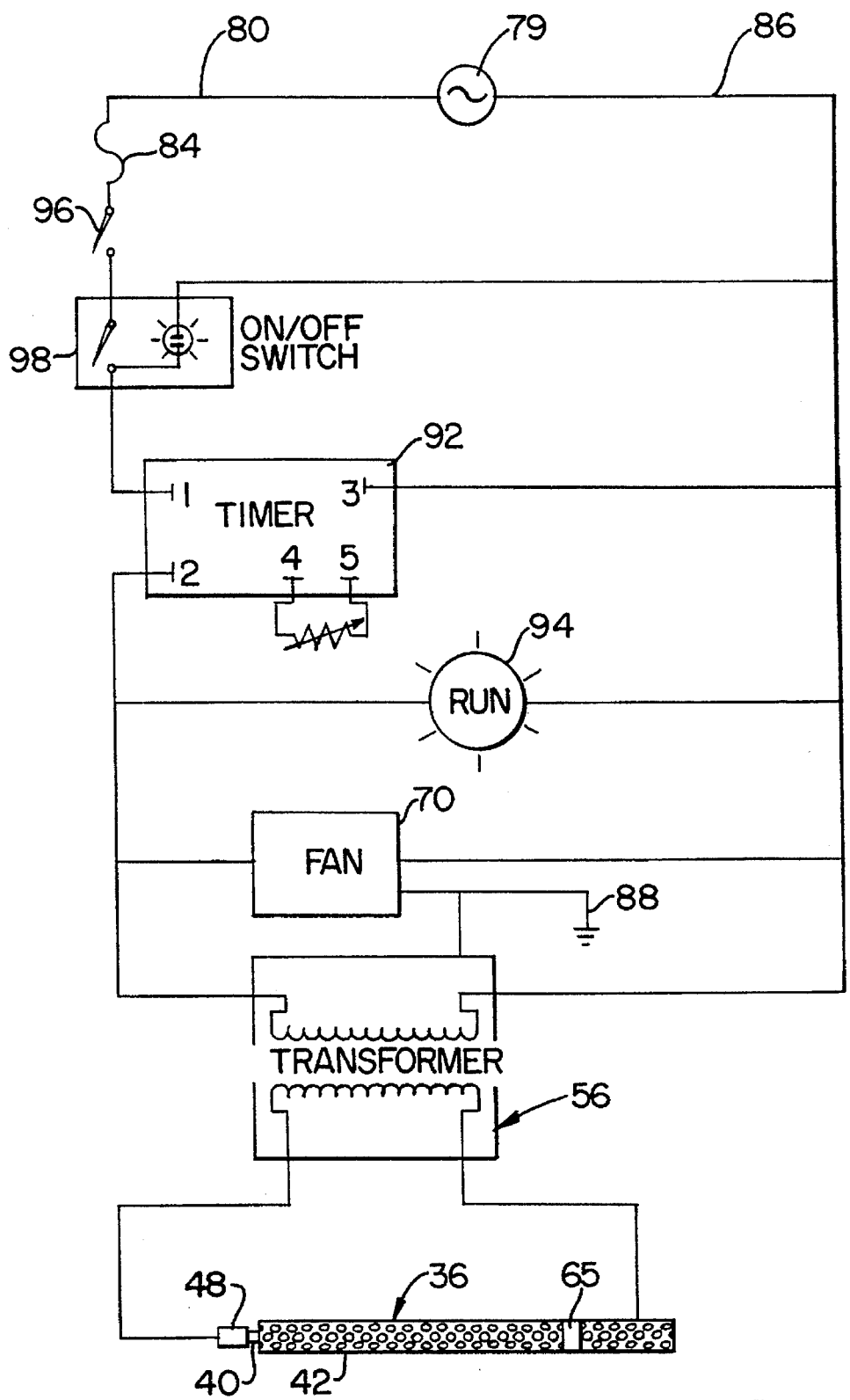
FIG. 3 is a simplified electrical schematic diagram for the apparatus of FIG. 1.

Turning now to a discussion of the electrical circuitry used for operating the unit, FIG. 3 illustrates in schematic form the wiring and electrically operated components for operation of the air purification unit. Power is supplied from a source 79 through a lead wire 80 of an electrical connector cord 82 (FIG. 1) through a fuse 84 and is returned through a neutral wire 86. Fuse 84 is a 1 ampere fuse designed to protect the electrical components from short circuits. Grounding for the transformer and fan is provided through a ground wire 88. The electrical connector cord 82 enters the side panel 24 (FIG. 1) through an orifice in the side panel and is protected by a strain relief bushing 90 from damage that otherwise could be caused by pulling on the cord.

A normally open mechanical safety switch 96 having a contact arm 97 is shown in FIG. 1 mounted to the underside of the supporting shelf 28 for the ozone generator. The power source 79 is electrically connected through the safety switch 96 to the circuitry in the unit and precludes operation of the unit unless the rear panel 22 is in place to close the switch. The safety switch contact arm must be closed by the rear panel before power can be supplied to an illuminated rocker switch 98 for operation of the unit. When the rear panel is secured in place on the housing, then the safety switch is closed and power is supplied to the rocker switch.

When the rear panel is in place and the rocker switch is depressed in the "on" position, internal contacts are closed, directing power through an electronic recycling timer relay represented at 92 and shown as having electrical contacts 1 through 5. Electronic timer relay 92 receives power from the rocker switch through contact 1 and provides power through contact 2 to a terminal strip 93 (FIG. 1) for variable and simultaneous on and off operation of the fan, the transformer, and a 120 volt run light 94. The terminal strip is also electrically connected to negative contact 3 on the timer relay. The electronic timer relay controls predetermined, time averaged concentrations of ozone in the surrounding atmosphere depending on the concentration of ozone produced during the on cycle.

The electronic timer shown provides variable periods of operation of the transformer of from 0.1 to 10 minutes with a fixed off period of 10 minutes. Electronic timers providing variable off periods are somewhat more expensive and are not necessary for successful operation of the apparatus in normal situations.

The timer is operated by use of a potentiometer, represented as contacts 4 and 5 on timer circuit 92, to provide variable and continuous timer control. Potentiometer control knob 95 is shown on side panel 24 (FIG. 1) for operator control of the timer relay.

When the air purifier rocker switch is turned on, the timer receives power through contact 1 and immediately begins timing an on time that is adjusted by turning the knob 95 to select a value for the potentiometer that corresponds to the amount of time that the air purifier is to generate ozone. At the end of the prescribed time, internal contacts open so that no power is supplied to contact 2 on the timer or distributed through the terminal strip to the fan, run light, and transformer. The air purifier shuts down while the timer cycles through its preset, fixed, 10 minute off cycle. At the end of the off cycle, the timer cycles to re-energize all functions through the terminal strip, provided that the contacts, the main switch, and the safety switch remain closed. The on and off sequence continues until the main switch is turned off or the primary circuit is interrupted by the safety switch, a blown fuse, or some other electrical failure.

EXAMPLE

An air purifying unit as described above and as represented in the drawings, having a transformer generating a secondary output voltage of about 9,000 volts at a secondary output frequency of about 400 to 500 Hz, having an air flow of about 57 cfm, and having an ozone generator as described, was placed on a high shelf in a modestly contaminated room of dimensions about 15'×22'×10' with minimal air circulation in the room. The unit was plugged into a standard 120 VAC 60 cycle grounded wall outlet and the rocker switch was moved to the on position. The run light indicated that ozone was being produced. The timer was set so that the generator produced concentrations of ozone at the outlet of about 1 ppm for periods of about 1 minute, alternating with periods of no ozone generation for a period of about 10 minutes. Ozone concentration was determined using a conventional ozone meter. The skilled artisan should recognize that a variety of such meters are available.

The ozone concentration at the outlet of the unit diminished rapidly on mixing with room air to a concentration of about 0.3 ppm at a distance of 2 feet from the outlet. Time averaged concentration of ozone in the air in the room as measured in the approximate center of the room was no more than 0.1 ppm over an 8 hour period.

It should be recognized that ozone production and the time averaged concentration of ozone are variable depending upon prevailing conditions and can be varied by the operator. Operation of the unit as described in the example typically results in levels of ozone at a distance of about 2 feet from the outlet of the unit of from about 0.2 to 0.4 ppm while ozone is being generated. These levels are suitable for purifying room air at commonly encountered contaminant levels for regularly occupied spaces and can provide a time averaged concentration of ozone in the area being treated that is suitable for continual occupancy.

Ozone has a pleasant and clean smell at the concentrations normally used to treat occupied spaces according to the apparatus of the invention. If excess ozone is being produced, then an operator can control the on cycle to reduce the time average concentration of ozone.

It should be recognized that rooms of different sizes or more contaminated rooms may result in increased time averaged ozone concentration for suitable ozone treatment. For rooms smaller than about 3300 ft$^3$ or for treating more heavily contaminated rooms at higher time averaged $O_3$ concentrations, it may be desirable to evacuate the room before using the apparatus. At high concentrations ozone has a pungent odor and can irritate the eyes and mucosa. After treatment at higher ozone levels, adequate ventilation typically should be provided prior to occupation of the room by persons or animals.

It should also be recognized that with a suitable timer an operator can vary the on time and the off time to increase or reduce the level of ozone treatment depending on prevailing conditions. Voltage can be set to control the concentration at which the ozone is produced at a level of from about 0.5 to 8.0 ppm and to increase or reduce the concentration of ozone at the outlet to the unit. Typically, the voltage will be set by the manufacturer or the unit and not by the operator since high voltages of 8,000 to 12,000 volts normally are used to generate ozone.

The invention claimed herein has been described with respect to a specific embodiment illustrated in the drawings. However, the foregoing description is not intended to limit the invention to the illustrated embodiment, and the skilled artisan should recognize that variations can be made within the spirit and scope of the invention as described in the foregoing specification. The invention includes all alternatives, modifications, and equivalents that may be included within the spirit and scope of the invention as defined by the appended claims.

What is claimed is:

1. Apparatus for treating air with ozone comprising:
   a) a housing having an air inlet and an air outlet and defining therebetween a passageway for the passage of air through said apparatus;
   b) means for drawing surrounding air through said passageway from said inlet to said outlet and discharging the air through said outlet into the surrounding air; and
   c) means for continually introducing ozone into the air in said passageway for discharge with the air through said outlet at a predetermined first concentration of ozone in the air, wherein said ozone introducing means comprises a corona generator located in said passageway, a transformer electrically connected to said corona generator and having a predetermined constant output voltage of from about 8,000 to 12,000 volts, and means for controlling the interval of time over which said ozone generator generates ozone for introduction into the air.

2. An apparatus according to claim 1 wherein said corona generator comprises a cathode tube electrically connected to said transformer and a perforated jacket anode circumscribing said corona tube and electrically connected to said transformer.

3. An apparatus according to claim 1 wherein said means for controlling the interval of time over which said ozone generating means generates ozone for introduction into the air comprises an on/off cycling timer relay electrically connected to said transformer for cycling said transformer on and off at predetermined intervals.

4. An apparatus according to claim 3 wherein said relay controls the on cycle at a predetermined time of from about 30 seconds to 10 minutes and the off cycle at a predetermined time of from about 5 minutes to 30 minutes.

5. An apparatus according to claim 1 wherein said predetermined first concentration is from 0.5 to 8 ppm of ozone in the air.

6. An apparatus according to claim 1 wherein said means for drawing air through said passageway from said inlet to said outlet and discharging air enriched in ozone through said outlet comprises a fan located in said inlet and drawing air through said inlet into said passageway and discharging the air through said outlet.

7. An apparatus according to claim 6 wherein said fan draws air into said inlet at the rate of from about 25 to 150 cfm.

8. An apparatus according to claim 1 wherein said means for continually introducing ozone into the air in said passageway for discharge with the air through said outlet at a predetermined first concentration of ozone in the air includes introducing ozone at an average concentration over time of ozone in the surrounding air that is not more than a predetermined average concentration, and introducing ozone at a concentration of ozone in the surrounding air during ozone introduction that is not more than a predetermined second concentration at a distance of not less than a predetermined distance from the housing.

9. An apparatus according to claim 8 wherein said predetermined first concentration is from about 0.5 to 2.0 ppm, said predetermined average concentration is not more than 0.1 ppm of ozone in the surounding air, and said predetermined second concentration is from 0.2 to 0.4 ppm at a distance from the housing of not less than 2 feet.

10. Apparatus for treating air with ozone comprising:
    a) a housing having a first compartment and a second compartment and having in said first compartment an air inlet for surrounding air and an air outlet and defining therebetween a passageway for the passage of air through said first compartment;
    b) a fan located in said inlet and drawing air through said inlet into said passageway and discharging air through said outlet at the rate of from about 25 to 150 cfm;
    c) an ozone generator mounted in a fixed location in said passageway, said ozone generator comprising a corona tube first electrode and circumscribed by a second electrode to create an annular space therebetween for the passage of air and for producing ozone at a predetermined first concentration of from 0.5 to 2.0 ppm of ozone in the air;
    d) a transformer located in said second compartment, said transformer having a predetermined constant secondary output voltage of from about 8,000 to 12,000 volts and being electrically connected to said first and second electrodes on said ozone generator to supply electricity to said generator at said output voltage; and
    e) an on/off cycling timer relay electrically connected to said transformer for cycling said transformer on and off at predetermined intervals, said relay controlling the average concentration over time of ozone in the surrounding air at a predetermined average concentration of not more than 0.1 ppm over an 8 hour period.

* * * * *